United States Patent [19]

English et al.

[11] 4,349,628
[45] Sep. 14, 1982

[54] FERMENTATION PROCESS FOR THE MANUFACTURE OF AN ORGANIC COMPOUND

[75] Inventors: Martin English, Ashtead; David P. Pym, Tadworth; Lindsay G. Dawson, Loughborough, all of England

[73] Assignee: Kins Developments Limited, London, England

[21] Appl. No.: 169,186

[22] Filed: Jul. 15, 1980

[30] Foreign Application Priority Data

Jul. 18, 1979 [GB] United Kingdom ................. 7924957
May 19, 1980 [GB] United Kingdom ................. 8016470

[51] Int. Cl.$^3$ .......................... C12P 7/06; B01D 3/42; C12M 1/02
[52] U.S. Cl. .................................... 435/161; 435/163; 435/165; 435/164; 435/316; 202/180
[58] Field of Search ............... 435/161, 162, 163, 165, 435/316; 202/180

[56] References Cited

U.S. PATENT DOCUMENTS

| 419,332 | 1/1890 | Horne | 435/162 |
|---|---|---|---|
| 2,206,024 | 8/1937 | Brown | 435/165 |
| 2,440,925 | 4/1944 | Boeckeler | 435/162 |
| 3,972,775 | 9/1976 | Wilke et al. | 435/163 |
| 4,009,075 | 2/1977 | Hoge | 435/165 |

FOREIGN PATENT DOCUMENTS 2432547  4/1980  France ................................. 202/180

OTHER PUBLICATIONS

Cysewski et al., Process Design and Economic Studies of Alternative Fermentation Methods for Production of Ethanol, Biotechnology and Bioeng., vol. XX, pp. 1421-1444 (1978).

*Primary Examiner*—Raymond N. Jones
*Assistant Examiner*—John E. Tarcza
*Attorney, Agent, or Firm*—Burns, Doane, Swecker & Mathis

[57] ABSTRACT

A process for the manufacture of ethanol or a like volatile organic compound by fermenting a carbohydrate with a micro-organism which will convert the carbohydrate into ethanol or a like volatile organic compound, continuously transferring a portion of the fermentation medium to a separator where ethanol or the like volatile organic compound is evaporated from the fermentation medium at a temperature which is not deleterious to the micro-organism by subjecting the fermentation medium to a reduced pressure and recycling part or all of the remaining fermentation medium to the fermenter, the rate of the circulation of fermentation medium from the fermenter to the separator and back being such that the amount of ethanol or like volatile organic compound in the fermentation medium in the fermenter is kept sufficiently low so as not to detrimentally affect the rate of fermentation, compressing the vapor issuing from the separator thereby raising its temperature, and recondensing the compressed vapor in a heat transfer system to provide heat for use in evaporating ethanol or the like volatile organic compound from the fermentation medium in the separator.

28 Claims, 2 Drawing Figures

FERMENTATION PROCESS FOR THE MANUFACTURE OF AN ORGANIC COMPOUND

FIELD OF THE INVENTION

The present invention relates to a process for the manufacture of ethanol or a similar volatile organic compound by the fermentation of a carbohydrate with a micro-organism.

DESCRIPTION OF THE PRIOR ART

It is known to manufacture ethanol and certain other volatile organic compounds such as isopropanol, butanol and acetone by the fermentation of a suitable carbohydrate-containing feedstock. Examples of feedstocks which are suitable for the production of ethanol by yeast fermentation are cane sugar, sugar beet, molasses, grain, potatoes, cassava and sweet sorghum.

In general, the product of such fermentation processes, once it reaches a particular concentration in the fermentation medium, exhibits a toxic effect on the micro-organism which is responsible for its production. For example, concentrations of ethanol greater than 8 to 10 v/v % can have a deleterious effect on yeast, so that the efficiency of production of ethanol falls as the ethanol concentration rises above this level. As a result, the known fermentation processes have to be performed in relatively dilute solutions. This leads to a number of drawbacks. For example, these processes have effluent problems because of the large amount of water which has to be disposed of, some of which is contaminated. Furthermore they also consume relatively high amounts of energy because of the need to recover alcohol from solutions of low concentration. Also the need to allow the fermenting materials to remain in the production plant for relatively long periods leads to high capital costs for equipment.

Methods which overcome some of these drawbacks have been suggested. For example, U.S. Pat. No. 2,440,925 describes a method of manufacturing ethanol by fermentation in which a stream of fermentation medium is withdrawn from the vessel in which the fermentation is performed and the stream is then subjected to a reduced pressure in a separate vessel in order to evaporate off the ethanol in the stream. However, such a method still has the drawback that it is wasteful of energy resources.

BRIEF SUMMARY OF THE INVENTION

An object of the present invention is to provide a process for the production of ethanol which affords a substantial reduction in the amount of energy which is wasted in performing the process. A further object of the invention is to provide a process in which a relatively smaller volume of water has to be discarded as effluent during performance of the process.

According to one aspect of the present invention there is provided a process for the manufacture of ethanol or a like volatile organic compound which process includes the steps of fermenting in a fermenter a carbohydrate with a micro-organism which will convert the carbohydrate into ethanol or a like volatile organic compound, continuously transferring a portion of the fermentation medium to a separator where ethanol or the like volatile organic compound is evaporated from the fermentation medium at a temperature which is not deleterious to the micro-organism by subjecting the fermentation medium to a reduced pressure and recycling part or all of the remaining fermentation medium to the fermenter, the rate of the circulation of fermentation medium from the fermenter to the separator and back being such that the amount of ethanol or like volatile organic compound in the fermentation medium in the fermenter is kept sufficiently low so as not to detrimentally affect the rate of fermentation, compressing the vapour issuing from the separator thereby raising its temperature, and recondensing the compressed vapour in a heat transfer system to provide heat for use in evaporating ethanol or the like volatile organic compound from the fermentation medium in the separator.

In a preferred embodiment of the process of the present invention, the process further includes the step of subjecting the vapour emanating from the separator to a fractional distillation under reduced pressure thereby to separate the components of the vapour. Preferably heat for use in the fractional distillation of the vapour is supplied by recondensing in a heat transfer system compressed vapour derived from the separator.

In one embodiment of the present process, the compressed vapour, before recondensation, is passed through a desuperheater to lower its temperature to a temperature below that at which the micro-organism will rapidly become inactive, but above that of the liquid leaving the fermenter. The lowering of the temperature of the compressed vapours may be performed by spraying a quantity of condensed volatile organic product into the compressed vapour, or by passing the vapours through a heat-transfer system where they give up some of their heat content.

When the fermentation is carried out by yeast, it is preferably performed at 15° to 45° C., more preferably 35° to 41° C.

To keep the running costs down to a minimum, the temperature of the stream of fermentation liquor entering the separator should be as high as possible. However this temperature is limited by the ability of the yeast or other micro-organism to survive. Thus, for example, it appears that currently known yeasts when producing ethanol will not tolerate temperatures higher than 45°–47° C. Consequently, when producing ethanol using a yeast the maximum temperature of the stream of fermentation liquor entering the separator is generally about 47° C., and the rate of circulation of fermentation medium and other variables has to be chosen accordingly.

Should one wish to produce ethanol having a concentration of 96% by weight or more from the top of the fractionating column without incurring higher costs in operating the plant, the fermentation must usually be performed at a temperature of 30° C. or more. Accordingly, when ethanol of a purity of 96% by weight or more is required, the fermentation is preferably performed at a temperature of 30° to 47° C., more preferably at a temperature of 35° to 41° C.

The raw material for the process of the present invention can be any source of carbohydrate material which can be used as a source of sugars, either as a direct source of sugar, or as a material which provides sugar by degradation of starch, cellulose, or other polysaccharides. Thus, examples of suitable sources of raw materials are crops such as sugar cane, sugar beet, fodder beet, molasses, grain, potatoes, cassava and sweet sorghum. Crops are desirably harvested before they contain substantial amounts of lignin, since lignin is difficult to break down into its constituent sugars. Saccharification of cellulose-containing feedstocks by one or more enzymes such as cellulase will also produce a suitable raw material; paper-waste products, wood and wood wastes are examples of cellulose-containing feedstocks.

In one embodiment of the invention the fermentation is carried out by using a strain of *Saccharomyces cerevisiae*, preferably in a concentration of 10 to 125 g dry weight per liter. The rate of recirculation can be varied depending on various factors but will generally be within the range of from 100 to 100,000 liters per minute, preferably 5000 to 40,000 liters per minute.

According to a further aspect of the present invention there is provided apparatus for performing the present process, said apparatus comprising a fermenter for performing the fermentation of a carbohydrate with a micro-organism to form ethanol or a like volatile organic compound, a separator in which ethanol or the like volatile organic compound can be evaporated from the fermentation medium, means for transferring fermentation medium from the fermenter to the separator and for recycling the said medium to the fermenter, a compressor for compressing the vapour issuing from the separator, and a heat-transfer system downstream of the compressor adapted and arranged to transfer heat for use in evaporating ethanol or the like volatile organic compound from the fermentation medium in the separator.

In one preferred embodiment of the present apparatus, the apparatus includes a fractional distillation column downstream of the separator and upstream of the compressor.

When using strong feedstocks such as molasses, generally one compressor is used, but when working with weak feedstocks which contain a higher proportion of water, although the use of one compressor is currently cheaper in terms of cost, the use of two compressors currently provides the greater saving in energy. Generally, when two compressors are used, one is used as a main compressor to provide a source of heat for evaporation of alcohol from the fermentation medium in the separator and for the distillation, while the other compressor is used to boost the pressure of some of the vapour issuing from the main compressor which vapour is then used as a source of heat for stripping residual alcohol from the aqueous liquor which has passed through the separator before it is discarded as effluent.

The process and apparatus of the present invention are particularly suitable for the production of ethanol using a yeast fermentation process, but it is envisaged that they are also suitable for the preparation of products such as isopropanol, butanol or acetone using other fungal fermentations or bacterial fermentations.

BRIEF DESCRIPTION OF THE DRAWINGS

The present invention will now be described, by way of example only, with reference to the accompanying drawings, in which.

DETAILED DESCRIPTION

Although the invention will be described with particular reference to a plant for the manufacture of ethanol using a yeast as the micro-organism, it is believed that the invention is also suitable for the preparation of other alcohols and ketones such as butanol, isopropanol and acetone from appropriate feedstocks using suitable micro-organisms.

Figure 1:
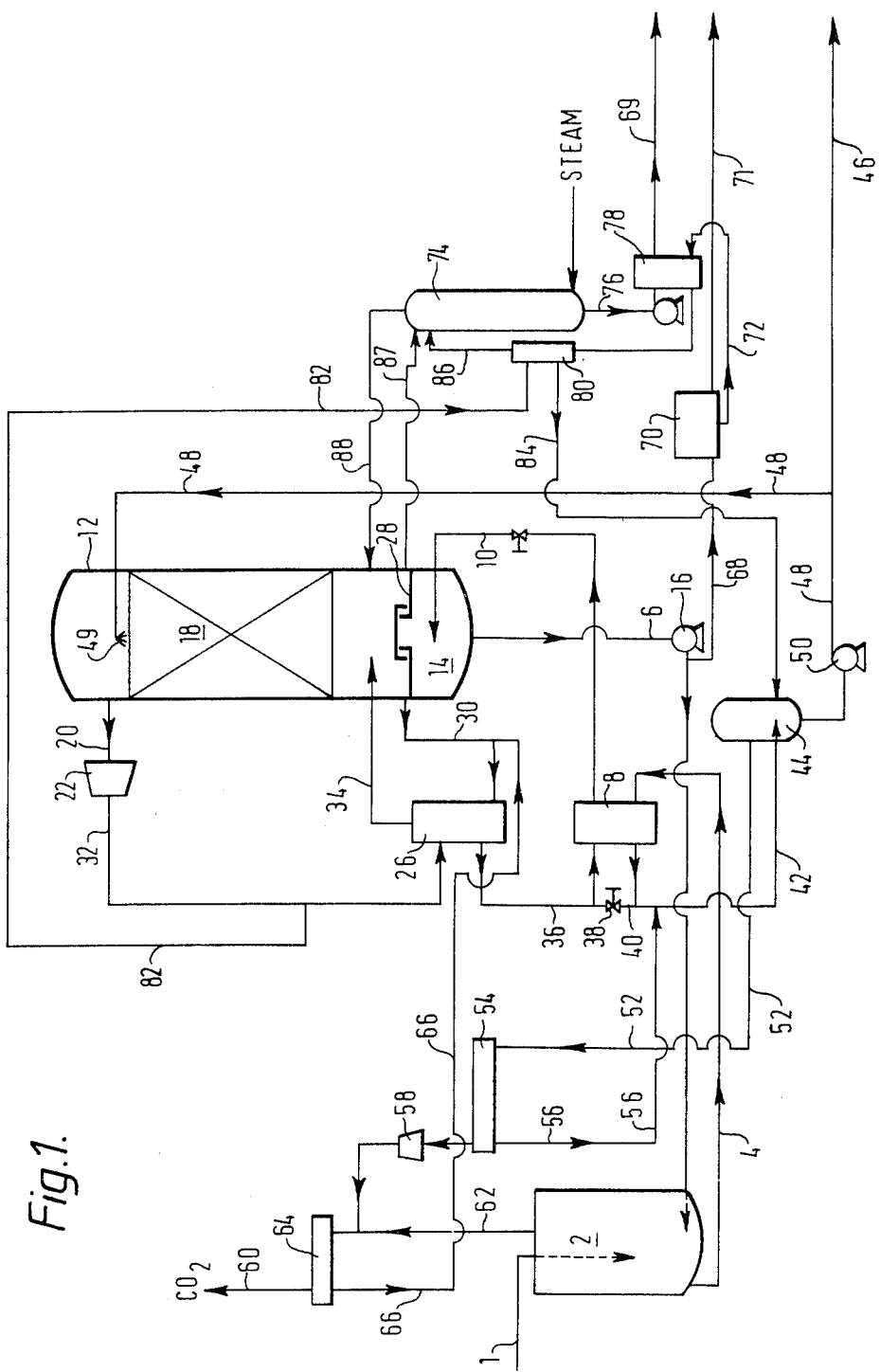
FIG. 1 is a flow diagram of a plant suitable for performing a process in accordance with the present invention.

Referring to FIG. 1, when the plant is in operation, a supply of carbohydrate raw material containing a chosen amount of a yeast which will convert the carbohydrate into ethanol to give a high yield at the highest appropriate temperature without economically deleterious effects, is fed as an aqueous medium through a supply line 1 to a fermenter 2 where the sugar is fermented in known manner at 35° to 41° C. to produce ethanol.

In order to avoid the need to dilute the feedstock to a standard concentration as in prior art processes, a stream of fermentation medium is withdrawn from the fermenter via line 4, ethanol is removed from the stream under reduced pressure at a separator 14, and then a portion of the stream is returned to the fermenter via line 6. In this way one is able to maintain an optimum concentration of ethanol in the fermenter corresponding to the maximum concentration of ethanol affecting the acceptable performance of the yeast. This optimum concentration of ethanol is normally 8 to 12 vol/vol %. Moreover, this arrangement allows the yeast to be re-used and reduces the throughput of water in the plant.

In order to separate the ethanol from the withdrawn stream of fermentation medium, the stream is first passed through a heat-exchanger 8, where it receives a first supply of heat which raises the temperature of the medium to a temperature which is below that at which the yeast is rapidly rendered inactive (e.g. below about 47° C.), but which is such that subsequent evaporation of ethanol at a reduced pressure will be facilitated. The way in which heat is supplied to the heat-exchanger 8 will be explained below. From heat-exchanger 8, the fermentation medium passes along a valved pipeline 10 into a separator 14 which acts as the bottom zone of the fractionation tower 12. The fractionation tower, including the separator, is maintained under a reduced pressure which enables a mixture comprising ethanol, water and carbon dioxide to be evaporated from the fermentation medium in the separator without raising the temperature of the medium to a temperature which will rapidly render the yeast inactive. In order to facilitate the evaporation of ethanol, the fermentation medium in the separator 14 preferably is agitated or is caused to move in a spiral so as to form a vortex. Spiral motion can be achieved for example by the use of a stirrer or by introducing the medium at a tangent to the side walls of the separator. The medium then passes out of the bottom of the separator 14 through line 6 and is returned to the fermenter 2. Circulation of the fermentation medium around the circuit formed by fermenter 2, line 4, heat-exchanger 8, line 10, separator 14 and line 6 is maintained by a pump 16.

The vapour mixture which is envolved in separator 14, which typically has an ethanol concentration of about 40% by weight, passes upwards into a fractionation column 18 containing a low pressure-drop contacting medium. An example of such a suitable contacting medium is crimped knitted steel wire such as the material sold by Metex Corporation of U.S.A. under the trade name Goodloe Column Packing.

Ethanol typically having a concentration of 96 to 98% by weight can be obtained at the top of the fractionation column by using an appropriately low pressure for the distillation. If ethanol of lower purity is desired, the pressure at the top of the column need not be lowered as much as is required to obtain high purity ethanol, or a column with less contacting medium or a less efficient separation medium can be used. The vapours obtained at the top of the fractionation tower are then led via line 20 to a compressor 22 and compressed. This compression step raises the temperature of the vapour, and the hot vapour is then used as a source of the heat required to separate the ethanol/water/carbon dioxide mixture from the fermentation medium and subsequently to fractionally distil this mixture. The bulk of the heat requirement of the mixture to be distilled is supplied to the mixture by contacting, in a heat-exchanger 26, the hot vapour issuing from the compressor via line 32, with a stream of liquid withdrawn via line 30 from a tray 28 immediately above the separator. Since the liquid which is to be heated in heat-exchanger 26 is "clean" liquid in the sense that it does not contain any substantial quality of microorganisms, the temperature of the compressed vapour in line 32 does not have to be lowered (i.e. desuperheated) before the vapour is introduced into the heat-exchanger 26. The stream of liquid heated in heat-exchanger 26 is returned via line 34 to the fractionation tower 12 and reintroduced into the tower at a position above tray 28. Loss of heat from the compressed ethanol vapour to the said stream of liquid causes ethanol vapour to condense. Heat-exchanger 26 is effectively acting as a desuperheater of the compressed vapour in line 32 by lowering its temperature to a temperature below that at which the yeast will rapidly become inactive, but above that of the liquid leaving the fermenter. The resultant stream of ethanol flows, via line 36, to the said first heat-exchanger 8, where by condensing and cooling it delivers to the stream of fermentation medium withdrawn from the fermenter the heat required to give the desired rate of evaporation of ethanol/water mixture in the separator 14. The temperature of the stream of ethanol entering the heat-exchanger 8 is below the temperature at which the yeast contained in the fermentation medium will rapidly become inactive so that the recirculated fermenter liquor on the other side of the heat exchanger 8 cannot be adversely affected by contact with too hot a surface. The proportion of ethanol in line 36 which flows through heat-exchanger 8 can be controlled by appropriately setting a valve 38 in a by-pass line 40. The condensed ethanol emanating from heat-exchanger 8 is conveyed along line 42 to a tank 44 from which purified ethanol is recirculated through the fractionation tower 18 in accordance with conventional fractionation techniques. The purified ethanol is recirculated by means of a pump 50 which drives the ethanol through line 48 to a distributor 49 at the top of the column 18. A portion of purified ethanol is removed from line 48 via line 46 to a reservoir (not shown) as the final product.

The upper zone of tank 44 communicates via line 52 with a condenser 54 which serves to condense the ethanol in the gas mixture present in the tank and return it to the tank along lines 56 and 42. Other gaseous components more volatile than ethanol, such as $CO_2$, are compressed to atmospheric pressure by a compressor 58 downstream of the condenser 54 and are released to the atmosphere via line 60, after having first been combined with the gaseous components emanating from the top of the fermenter 2 along line 62, and having been passed through a further condenser 64. This last condensation further minimizes losses of product to the atmosphere, the condensed product emanating from condenser 64 being conveyed along line 66 to join the product in line 30 entering heat-exchanger 26.

The less volatile components of the vapours issuing from the separator 14 collect at the bottom of the fractionation column 12 in tray 28. Excess of the liquid in tray 28 is withdrawn along line 87 and is conveyed to the top of a stripping column 74 (described in more detail below) where residual ethanol in the liquid is stripped therefrom prior to the aqueous residue being described as effluent via line 69.

In order to compensate for the water and other unconvertable products being added to the fermenter 2, some of the fermentation medium issuing from the separator 14 is tapped off along line 68. Before being discarded as effluent along line 69, this material is treated to recover the excess yeast and ethanol which it contains. Thus, the material drawn off along line 68 passes through a filter or centrifuge 70 where the yeast is removed, and the yeast balance is maintained by recirculating yeast as required to the fermenter, the remainder being moved from the system. The filtrate or supernatent is then subjected to a fractional distillation or stripping to recover ethanol.

In order to perform the fractional distillation or stripping, the filtrate or supernatent passes along line 72 through a first heat-exchanger 78 where it receives heat from the liquid effluent emanating along line 76 from the bottom of a stripping column 74. The filtrate then passes from the heat-exchanger 78 to a further heat-exchanger 80 where it receives a further quantity of heat from a side-stream 82 of hot ethanol vapour taken from line 32 downstream of the compressor 22. After leaving the heat-exchanger, the side-stream 82 of ethanol is conveyed via line 84 to tank 44, while the filtrate leaving the heat-exchanger along line 86 is fed to an inlet point near the top of the stripping column 74. The vapours emanating from the top of the column 74 are conveyed, via line 88, to the fractionation tower 12 and introduced into it at the foot of the fractionation column 18. For strong feedstocks such as molasses and cane syrup and feedstocks derived from cassava, steam is generally used to supply the heat required for the fractional distillation. However, in the case of weak feedstocks such as cane sugar and sugar beet which contain a larger percentage of water and therefore lead to greater quantities of aqueous effluent which has to be stripped of its residual alcohol, more energy can be saved by obtaining the heat for the fractional distillation not from steam but by passing the vapours issuing from the top of stripping column 74 through a compressor. This results in the temperature of the vapours rising, and the heated vapours are then passed through a heat-exchanger where heat is transferred to liquid taken from, and then recycled to, the foot of the stripping column 74. The vapours passing through this last heat-exchanger, having lost the bulk of their heat are then conveyed to the foot of the fractionation column 18.

Although the plant described above includes two separate heat-exchangers 26 and 8 in which heat is transferred to the ethanol to be separated and distilled, heat-exchanger 26 being used on "clean" liquid and heat-exchanger 8 being used on fermentation medium containing yeast, it is possible to use an arrangement in which only one heat-exchanger is used to perform this heat-transfer, in which case heat is transferred only to the fermentation medium containing yeast. When this is done it is necessary to desuperheat the compressed vapour issuing from compressor 22 to lower the temperature of the vapour to a temperature below that at which the yeast rapidly becomes inactive, but above that of the liquid medium leaving the fermenter. This desuperheating is conveniently performed by spraying a quantity of the condensed ethanol into the compressed vapour flowing in line 32.

It should be understood that if alcohol of a purity no greater than about 40% w/w is acceptable, the distillation column 18 need not be included in the plant. The vapours which issue from separator 14 which have an ethanol content of about 40% w/w can, after passing through an appropriate washing system, themselves be compressed directly and then passed through a heat-transfer system as described above. However, if alcohol of a purity greater than 40% w/w is desired, a fractionation column must be included downstream of the separator.

Figure 2:
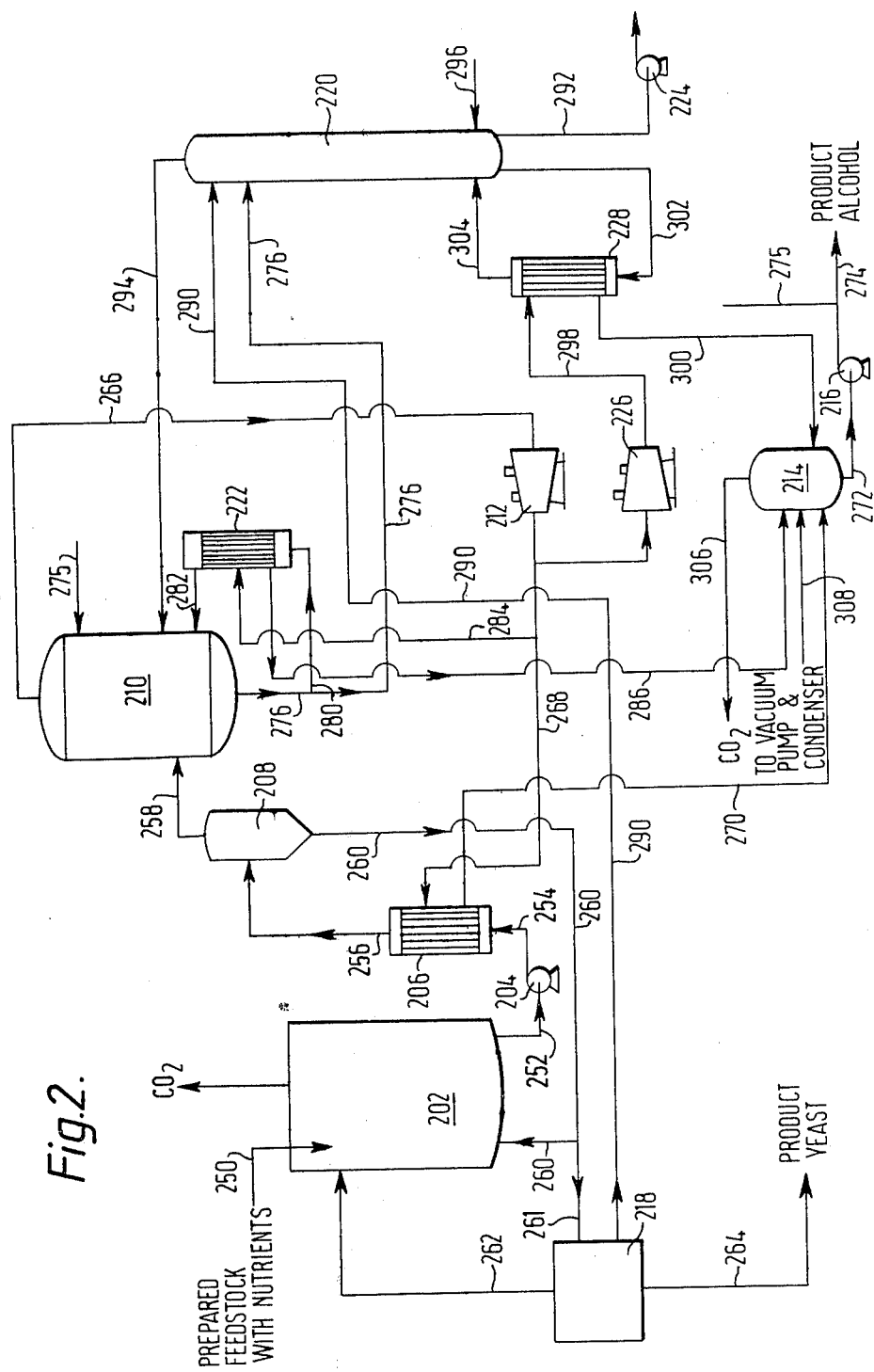
FIG. 2 is a similar flow diagram of an alternative plant for performing a process in accordance with the present invention.

Referring now to FIG. 2, there is shown a slightly modified plant for performing the process of the present invention. In many respects this alternative arrangement is similar to the plant shown in FIG. 1, the main differences being that the separator 208 in this plant is separate from the rectifying or distillation column 210, and that only one heat-exchanger 206 is used to transfer heat from the compressed vapours issuing from compressor 212 to the fermentation medium from which ethanol is to be evaporated. In addition this arrangement uses two compressors 212 and 226 rather than the single compressor 22 of the plant of FIG. 1. In general, for weak feedstocks use of one compressor is cheaper in terms of cost, but use of two separate compressors as shown in FIG. 2 provides the greater saving in energy.

The embodiments of FIG. 2 will first be described with reference to a plant for producing 100,000 liters per day of alcohol from sugar beet juice. A prepared feedstock of sugar beet juice, water, yeast and nutrients containing 15% by weight of fermentable sugars is fed through a supply line 250 at a rate of 1200 tonnes/day (t/d) into a continuous fermenter 202 having a capacity of 120 m³. In the fermenter 202 the sugars are fermented in known manner at a temperature of 35° to 41° C. to produce ethanol. A stream of the contents of the fermentation vessel, typically containing 6% wt/wt ethanol, is withdrawn therefrom via line 252, ethanol is removed from the stream by evaporation in a separator 208 and the remaining fluid is recycled to the fermenter via line 260. Circulation of the fluid from the fermenter 202 to the separator 208 and back again in maintained by a recirculation pump 204, typically having a capacity of 6400 l/min. The stream of fermentation medium withdrawn from the fermenter by the pump 204 passes via line 254 through a heat-exchanger 206 where its temperature is raised to about 40° C., and then is conveyed via line 256 to a separator or flash vessel 208 where a mixture comprising ethanol, water vapour and carbon dioxide is evaporated from the fermentation medium, the evaporation being performed under reduced pressure typically 0.09 bar, in known manner thereby enabling the temperature of the medium to be kept low enough to prevent the yeast from rapidly becoming inactive.

The residual liquid in the separator 208 is conveyed at a temperature of 35° to 37° C. back to the fermenter via line 260. In order to maintain the water balance in the fermenter 202, liquor is drawn off from the fermenter recycle circuit via line 261. Yeast is removed from the liquor at a yeast separation plant 218 and the clarified liquor then passes via line 290 to a stripping column 220 where its content of alcohol is removed before it is discharded as aqueous effluent via line 294, optionally to a biological treatment plant.

A portion of the yeast collected in the yeast separation plant 218 may be returned to the fermenter 202 to maintain the yeast concentration at a chosen level, the remainder being removed via line 264 as a by-product (typically an amount of 5 to 6 tonnes dry weight/day).

The mixture of vapours envolved in separator 208, generally containing approximately 40% by weight ethanol then passes along line 258 to a rectifying or fractional distillation column 210, which as before preferably contains a contacting medium which will afford efficient separation under reduced pressure of the components of the mixture of vapours. The vapours issuing from the top of the rectifying column 210, issue at a pressure of 0.06 bar and a temperature of 19.7° C. and typically contain 96 to 98% by weight ethanol, and are conveyed via line 266 to a main compressor (800 kW) 212 and compressed. Typically, this compression step raises the pressure of 96% w/w ethanol to approx. 0.30 bar at a saturation temperature of approximately 50° C. The resultant vapour is then conveyed to heat-exchanger 206 where it releases some of its heat content to the stream of fermentation medium entering the heat-exchanger via line 254. As has been indicated above, the temperature of the vapours entering the heat-exchanger 206 must be kept at a temperature below that at which the yeast in the fermentation liquor is rapidly rendered inactive. This is conveniently done by spraying a quantity of already purified ethanol into the compressed vapours in line 268. After passage through the heat-exchanger 206, the ethanol at a temperature of about 50° C., leaves the heat-exchanger via line 270, and is conveyed to a tank 214. Ethanol (96 to 98 wt %) issues from the plant via line 272, pump 216 and line 274 at the rate of approximately 100,000 liters/day (i.e. 79 t/d). A proportion of the purified ethanol is recirculated by pump 216 via line 275, to the top of the fractionation column 210.

The liquor which collects at the bottom of the rectifying column 210, which has been stripped of most of its alcohol, is withdrawn along line 276 and conveyed to the top of a stripping column 220, where any residual ethanol is stripped from the residual liquor. A proportion of the liquor which is withdrawn from the rectifying column 210 via line 276 is passed via line 280 to a reboiler 222 where it is heated by heat-exchanger with a fraction of the compressed ethanol taken from line 268, and is then recycled to the lower part of the rectifying column 210 via line 282. The said fraction of compressed ethanol is conveyed to the reboiler 222 from line 268 along line 284 and after passage through the reboiler is conveyed along line 286 to tank 214.

The liquor introduced along line 276 into the stripping column 220, together with yeast-free liquor from the yeast separation plant introduced into the stripping column via line 290 at the rate of about 40 m³/hour, is stripped of its residual ethanol content and is withdrawn as stillage via line 292 and pump 224 from the bottom of the column at a rate of about 1025 t/d. The heat required for the stripping column 220 is obtained either from an outside heat source such as steam (e.g. at the rate of 156 t/d) introduced via line 296 or by taking a proportion of purified compressed ethanol from line 268 and compressing it further in a stripper compressor (360 kW) 226. Typicaally this raises the saturation temperature of the vapour to about 70° C. (at a pressure of 0.80 bar). The compressed ethanol emanating from the stripper compressor 226 is passed via line 298 to a stripping column reboiler 228 where it delivers heat to a stream of fluid taken via line 302 from the lower region of the stripping column 220, the said stream of fluid returning to the stripping column via line 304 at a temperature of about 60° C. The ethanol passing out of the stripping column reboiler is then conveyed via line 300 to tank 214.

Ethanol and other vapours emanating from the top of the stripping column 220 are returned via line 294 to the rectifying column 210 for further purification.

Ethanol vapour and $CO_2$ which collect in tank 214 are conveyed by line 306 to a condenser system of the type shown in FIG. 1 where the ethanol is condensed and returned via line 308 to tank 214. The pressure of the carbon dioxide passing out of the said container is raised to atmospheric pressure and released to atmosphere at the rate of about 16 t/d.

The plant of FIG. 2 is also suitable for performing a process which produces 100,000 liters per day of 96% by weight ethanol from beet molasses. The process is performed as described above for the production of ethanol from sugar beet juice, but the following are typical operating conditions:

Rate of introduction of beet molasses feedstock (59% by weight sugars): 300 t/d
Recirculation rate of fermentation medium: 21,600 l/min
Main compressor (212): 800 kW
Stripper Compressor (226): 50 kW
Temperature and pressure of distillation products in line 226: 20.5° C. at 0.06 bar
Steam required for stripping column 220: 20 t/d
Rate of flow of fluid in line 290: 0.5 m³/h The products of the process are:
Ethanol (96% by wt): 100,000 liters/day
$CO_2$ in fermenter: 45 t/day
$CO_2$ from tank 214: 45 t/day
Stillage (from line 292): 126 t/day.

It should be understood that although in the processes described above for the production of ethanol the yeasts will not tolerate prolonged exposure to temperatures greater than 70° C., short exposure to temperatures higher than 50° C. will not generally have a seriously detrimental effect on the yeast. Generally speaking, the present process is performed in such a manner that the bulk of the yeast is at an average temperature not higher than about 47° C. even though some of the fermentation medium containing the yeast may be in contact for a short time with surfaces which are at a higher temperature of up to 70° C.

As has been shown above the present process is usually performed with apparatus incorporating either a single main compressor, or a main compressor together with an associated stripper compressor. The choice of whether or not to use a stripper compressor is governed by the relative savings obtained in the associated cost of the plant and in the energy expended. When weak feedstocks are used, these include a high proportion of water which leads to the need to dispose of relatively larger quantities of water. In such a case the cheapest energy solution is to use a main compressor to provide compressed vapour which can be used as a source of heat for the main ethanol separation and distillation, and a stripper compressor to take a portion of the compressed vapours and to raise them to a higher pressure, this vapour at higher pressure then being used as a source of heat for stripping residual ethanol from the aqueous liquid which is to be discarded as effluent from the plant. The cheapest solution as regards capital expenditure at the present time is the use of a single main compressor for providing heat for the main separation and distillation steps and to use steam as the source of heat for the stripping column.

With strong feedstocks where the amount of aqueous effluent to be stripped of ethanol is smaller, the second alternative mentioned above in which only a main compressor is used is preferred since the costs associated with generating steam for the stripping column are much the same as those associated with running the stripper compressor.

What we claim is:

1. A process for the manufacture of ethanol or a like volatile organic compound which process comprises the steps of fermenting in a fermenter a carbohydrate with a micro-organism which will convert the carbohydrate into ethanol or a like volatile organic compound, continuously transferring a portion of the fermentation medium, through a heat exchanger where it receives a supply of heat which raises the temperature of the medium to a temperature which is below that at which the micro-organism is rapidly rendered inactive, but which is such that subsequent evaporation of ethanol or the like volatile organic compound at a reduced pressure will be facilitated, to a separator where ethanol or the like volatile organic compound is evaporated from the fermentation medium at a temperature which is not deleterious to the micro-organism by subjecting the fermentation medium to a reduced pressure and recycling part or all of the remaining fermentation medium to the fermenter, the rate of the circulation of fermentation medium from the fermenter to the separator and back being such that the amount of ethanol or like volatile organic compound in the fermentation medium in the fermenter is kept sufficiently low so as not to detrimentally affect the rate of fermentation, subjecting the vapour issuing from the separator to a fractional distillation column containing a low pressure drop contacting medium under reduced pressure thereby to separate the components of the vapour, compressing the vapour issuing from the top of the fractionation distillation column thereby raising its temperature, recondensing the compressed vapour in a heat transfer system to provide heat, and using said heat both for evaporating ethanol or the like volatile organic compound from the fermentation medium in the separator and for said frictional distillation of the vapour.

2. A process according to claim 1, wherein the fermentation is performed at 15° to 45° C.

3. A process according to claim 2, wherein the fermentation is performed at 35° to 41° C.

4. A process according to claim 1, wherein the micro-organism is a strain of *Saccharomyces cerevisiae*.

5. A process according to claim 1, wherein the fermentation is performed using a yeast in a concentration of 10 to 125 g dry weight per liter.

6. A process according to claim 1, wherein the rate of recirculation of fermentation medium is from 100 to 100,000 liters per minute.

7. A process according to claim 6, wherein the rate of recirculation is from 5000 to 40,000 liters per minute.

8. A process according to claim 1, wherein the vapours issuing from the separator include 15 to 50% by weight ethanol.

9. A process according to claim 1, wherein the vapour issuing from the top of the fractionation column includes 80 to 99% by weight ethanol.

10. A process according to claim 9, wherein the vapour issuing from the top of the fractionation column includes 96 to 98% by weight ethanol.

11. A process according to claim 1, wherein the fractional distillation is performed with a pressure of 0.02 to 0.10 bar at the top of the column.

12. A process according to claim 1, wherein the liquor issuing from the bottom of the fractionation column is subjected to a subsequent stripping step to remove residual ethanol therefrom.

13. A process according to claim 12, wherein the ethanol vapour stripped from the said liquor is returned to the fractionation column for redistillation.

14. A process according to claim 1, wherein the vapour issuing from the top of the fractionation column is compressed in a single compression step to a pressure of 0.1 to 1 bar.

15. A process according to claim 1, wherein the vapour issuing from the top of the fractionation column is compressed in a first compression step to a pressure of 0.1 to 0.5 bar, and then a portion of said compressed vapour is subjected to a further compression step to compress the vapour to a pressure of 0.5 to 1 bar.

16. A process according to claim 15, wherein the vapour which has been subjected to said further compression step is passed through a heat-exchanger where it gives up some of its heat content to liquor taken from, and recycled to, the stripping column thereby to supply heat required for stripping ethanol from the said liquor.

17. A process according to claim 1, wherein the fractional distillation is performed in a distillation column located above the separator, both the said column and separator being housed within a common tower.

18. A process according to claim 1, wherein part of the fermentation liquor which has passed through the separator is not recycled but is withdrawn, yeast is removed therefrom and the resulting liquor is then subjected to a stripping step to remove ethanol therefrom.

19. A process according to claim 18, wherein some of the yeast removed from said liquor is recycled to the fermenter.

20. A process according to claim 18, wherein ethanol stripped from said liquor is returned to the fractionation column for redistillation.

21. A process according to claim 18, wherein some or all of the heat required to perform said stripping step is obtained from the vapours which have issued from the fractionation column and which have been compressed.

22. A process according to claim 1, wherein the vapours issuing from the fractionation column are compressed and before being recondensed, are passed through a desuperheater where their temperature is lowered to a temperature below that at which the micro-organism will rapidly become inactive, but above that of the liquid leaving the fermenter.

23. A process according to claim 22, wherein the temperature of the compressed vapours is lowered by passing the vapours through a heat-transfer system.

24. A process according to claim 22, wherein the temperature of the compressed vapours is lowered by spraying a quantity of condensed ethanol or the like volatile organic product into the compressed vapour.

25. A process according to claim 1, wherein the carbohydrate is a component of a feedstock derived from fodder beet, sugar cane, sugar beet, grain, potatoes, cassava or sweet sorghum.

26. A process according to claim 1, wherein the carbohydrate is a component of molasses.

27. A process according to claim 1, wherein the carbohydrate is a component of a cellulose-containing feedstock which has been saccharified.

28. A process according to claim 27, wherein the cellulose-containing feedstock is wood, wood wastes, bagasse, waste paper or paper-wastes.

* * * * *